United States Patent [19]

Yoshizumi et al.

[11] Patent Number: 4,670,255

[45] Date of Patent: * Jun. 2, 1987

[54] HAIR TONIC COMPOSITION

[75] Inventors: Hajime Yoshizumi, Takatsuki; Teruo Amachi, Takarazuka; Takaaki Kusumi, Suita; Takaharu Tanaka, Osaka; Hiroshi Ishigooka, Ibaraki, all of Japan

[73] Assignee: Suntory Limited, Osaka, Japan

[*] Notice: The portion of the term of this patent subsequent to Jan. 21, 2003 has been disclaimed.

[21] Appl. No.: 572,064

[22] Filed: Jan. 19, 1984

[30] Foreign Application Priority Data

Jan. 21, 1983 [JP] Japan ................................. 58-7463

[51] Int. Cl.$^4$ .................... A61K 37/00; A61K 37/48; A61K 7/06
[52] U.S. Cl. ........................................ 424/93; 424/92; 424/70; 424/95; 435/248; 435/243; 435/250; 435/882
[58] Field of Search ...................... 424/93, 92, 70, 94, 424/DIG. 4; 435/198, 189, 243, 248, 882, 883, 884, 250; 514/852, 881

[56] References Cited

U.S. PATENT DOCUMENTS 3,671,634 6/1972 Carlson et al. ...................... 424/274

OTHER PUBLICATIONS

Balsam et al., *Cosmetics Science and Technology*, Wiley Interscience, 1972, pp. 154–155.
Harry, *Volume Two, Cosmetic Materials*, Chem. Publishing Co., Inc., New York, N.Y., 1963, pp. 300–301, 308, 459.
Pablo et al., *Chem. Abst.*, vol. 83, No. 55140q, 1975, p. 205, "Characterization of the Extracellular Lipases from *Corynebacterium acnes* and *Staphyococcus epidermis*".
Pemice et al., *Chem. Abst.*, vol. 71, No. 119809b, 1969, p. 28, "Use of Tween 85 as a subtrate for the Determination of Lipase Activity in Bacteria".
Troller et al., *Chem. Abst.*, vol. 73, No. 105679p, p. 31, "Isolation and Characterization of Staphylococcal Lipase".
Hawley, *Condensed Chemical Dictionary*, 10th Edition, Van Nostrand Reinhold Co., 1981.
Kloos et al., *Chem. Abst.*, vol. 83, No. 4839s, 1975, "Isolation and Characterization of Staphylococci from Human skin. II. Description of Four New Species; Staphylococcus warneri . . . ", p. 431.
Sewell et al., J. Clin. Micro., vol. 16(2), Aug. 1982, pp. 236–239, "Clinical Significance of Coagulase-Negative Staphyllococci".

*Primary Examiner*—Lionel M. Shapiro
*Assistant Examiner*—Robin Lyn Teskin
*Attorney, Agent, or Firm*—Burns, Doane, Swecker & Mathis

[57] ABSTRACT

A hair tonic composition containing, as an effective ingredient, a product obtained from the interaction of a vegetable or animal fat or oil with a microorganism belonging to *Staphylococcus capitis*. This hair tonic composition can effectively prevent the generation of dandruff and itching and can also effectively accelerate the growth of hair.

8 Claims, No Drawings

HAIR TONIC COMPOSITION

BACKGROUND OF THE INVENTION

1. Field of the Invention

The present invention relates to a novel hair tonic composition suitable for use in preventing the generation of dandruff (or scurf) in hair and itching in the scalp. More specifically, it relates to a novel hair tonic composition containing, as an effective ingredient, products obtained from the interaction of a vegetable or animal fat or oil with a microorganism belonging to *Staphylococcus capitis*.

2. Description of the Prior Art

The possession of a healthy head of hair throughout life is the ambition of most human beings. Various kinds of hair dressings, including hair tonic compositions, have been used for alleviating or curing epilation or depilation (i.e., the involuntary loss of hair and subsequent balding). However, although various kinds of disease appear, such as alopecia, the causes thereof and the mechanisms thereof are not fully understood. It is considered that the epilation is correlated with abnormalities in the capillary vessels, hair follicles, and epidermis skin due to changes in, for example, the endocrine system, autonomic nervous system, and blood circulation system. Accordingly, to prevent or alleviate the above-mentioned abnormalities, various agents, for example, skin hyperergasia agents such as female hormones, vitamins, amino acids, crude drug extracts, various bactericides, keratolysis agents, and sensitizing dyes, and peripheral nervous stimulators such as menthol, have been used in the hair tonic composition. However, at present there are no truly effective agents for alleviating the epilation, accelerating the growth of hair, and further alleviating or curing the generation of dandruff in the hair and itching in the scalp.

SUMMARY OF THE INVENTION

Accordingly, an object of the present invention is to provide a novel hair tonic composition capable of effectively depressing the generation of dandruff and itching in the hair and scalp.

Other objects and advantages of the present invention will be apparent from the description set forth hereinbelow.

In accordance with the present invention, there is provided a hair tonic composition containing, as an effective ingredient, a product obtained from the interaction of at least one member selected from the group consisting of vegetable and animal fats and oils with a microorganism belonging to *Staphylococcus capitis*.

DESCRIPTION OF THE PREFERRED EMBODIMENTS

The inventors have previously found that, after making a detailed comparative study of the microflora of the scalps of persons with healthy hair and those of persons with unhealthy hair (e.g., the generation of dandruff and itching in the scalp and abnormal depilation), *Staphylococcus capitis* constitutes all or most parts of the microflora in the scalp of those with healthy hair. Contrary to this, no substantial amount of *Staphylococcus capitis* is found in the microflora, but microorganisms such as *Staphylococcus epidermidis* and *Pityrosporum ovale* are present as a main microflora phase instead of *Staphylococcus capitis*, in the scalp of those with unhealthy hair. Furthermore, the inventors have clarified that the cells of *Staphylococcus capitis* have a lipase activity and testosterone 5α-reductase (i.e., "5α-reductase") inhibitory activity. The term "5α-reductase" denotes an enzyme which reduces testosterone to 5α-dihydrotestosterone. Based on these findings, the inventors have suggested that the above-mentioned activities are closely correlated with the growth effect of hair (see U.S. patent application Ser. No. 505,273 or European patent application No. 83303654.4).

The inventors have further found that, when the correlation of the above-mentioned lipase activity and 5α-reductase inhibitory activity with the hair growth effect is studied in detail, products containing fatty acids, as a main constituent, obtained from the interaction of lipase from *Staphylococcus capitis* with fats and oils, have a strong 5α-reductase inhibitory activity. Based on this new finding, the inventors have found that the products obtained from the interaction of fats and oils with *Staphylococcus capitis* alleviate dandruff and itching.

The microorganisms or cells used in the present invention are those belonging to the species *Staphylococcus capitis*. These microorganisms can be selected from the natural occurring microorganisms, for example, from the scalp, or artificial or natural mutants thereof. Typical examples of these microorganisms are those deposited in the American Type Culture Collection (A.T.C.C.) (Rockville, Md., U.S.A.) as ATCC-27840 to ATCC-27843, as listed in the brochure published in 1982 by the ATCC. These microorganisms are freely available from ATCC.

If the microorganisms used in the present invention are desired to be freshly isolated from, for example, the scalp in healthy condition, any conventional manner known in the art can be used. Furthermore, if the mutants thereof are desired to be obtained, any conventional mutation means can be used in the present invention.

The fats and oils used in the present invention are those which can produce, upon interaction with *Staphylococcus capitis*, products having an effect on the hair growth. Examples of these fats and oils are vegetable oils such as olive oil, castor oil, cotton seed oil, coconut oil, soybean oil, palm oil, safflower oil, colza oil, rice bran oil, tsubakil oil (camellia oil), and sesame oil, and animal fats and oils such as tallow, lard, mutton tallow, mink oil, and whale oil. These fats and oils can be used alone or in any mixture thereof.

The methods for interacting the fats and oils with the microorganisms belonging to *Staphylococcus capitis* are not specifically limited. However, the following methods can be conveniently used from the practical point of view.

(1) *Staphylococcus capitis* is cultured in a culture medium containing the fats and oils;

(2) *Staphylococcus capitis* is cultured in a culture medium and the cultured cells of *Staphylococcus capitis* are then brought into contact with the fats and oils in an aqueous medium; or (3) The above-mentioned methods (1) and (2) are combined.

When the above-mentioned method (1) is used, any culture condition under which *Staphylococcus capitis* grows well can be used without limitation. Any nitrogen source which can be utilized by *Staphylococcus capitis* is used as a nitrogen source in the culture medium. Preferable examples of the nitrogen sources are organic nitrogen sources, for example, protein decomposition products such as casein peptones, soybean peptones, tripticase peptones, and casamino acids; extracts such as meat extracts and yeast extracts; soybean cake; and amino acids. Inorganic nitrogen sources such as ammonium salts and nitrates are optionally used.

Any carbon source which can be utilized by *Staphylococcus capitis* is used as a carbon source in the culture medium. Typical examples of such carbon sources are glucose, fructose, mannose, and glycerine. Furthermore, inorganic salts such as phosphates, hydrochlorides, magnesium salts, potassium salts, and sodium salts; vitamines; amino acids; or growth factors containing a large amount of these substances may be optionally used in the culture medium, depending upon the selection of the nitrogen sources.

In general, the above-mentioned nitrogen sources and carbon sources are independently used in a concentration of 0.1 g/liter to 100 g/liter, respectively, in the culture medium, depending upon the types of nitrogen and carbon sources. Furthermore, the above-mentioned inorganic salts and growth factors are generally used in a concentration of 0.01 g/liter to 50 g/liter, respectively, in the culture medium, depending upon the types of inorganic salts and the growth factors. The cultivation temperature is generally 20° C. to 40° C., preferably 32° C. to 37° C. The cultivation is generally effected at a pH of 6 to 9, preferably under aerobic conditions by, for example, a shaking culture or an aeration agitating culture. The cultivation time is generally 20 to 45 hours. The desired cultivation can be directly carried out. However, it is desirable that the precultured products obtained from a small scale preculture are inoculated into a culture medium.

The cultivation is effected by adding the above-mentioned fats and oils to the culture medium. The above-mentioned fats and oils can be contained in the culture medium prior to the cultivation or can be added to the culture medium during the cultivation after a certain amount of the cells is proliferated. The amount of the fats and oils is generally 1 g/liter to 250 g/liter, preferably 5 g/liter to 50 g/liter.

When the above-mentioned method (2) is used, the *Staphylococcus capitis* is cultured in the same manner as mentioned in method (1), except that no fats and oils are added to the culture medium. After the cultivation is completed, the cultured cells are brought into contact with the above-mentioned fats and oils. The contact of the cultured cells with the fats and oils can be most simply carried out, while appropriately stirring, after adding the fats and oils to the culture medium containing the cultured cells of *Staphylococcus capitis*. However, if it is necessary to remove the medium components from the cultured *Staphylococcus capitis*, the cells of *Staphylococcus capitis* are isolated from the cultured mixture by any conventional method, and the isolated cells are then suspended in an appropriate aqueous medium, for example, in a phosphate buffer solution, followed by the addition of the fats and oils. The pH and temperature conditions during the contact of the cells with the fats and oils are those within the ranges of the above-mentioned culture of *Staphylococcus capitis*.

The hair tonic composition according to the present invention contains, as an effective ingredient, the interaction products of the *Staphylococcus capitis* with the fats and oils mentioned above. The interaction products can be incorporated into the hair tonic composition in various embodiments. Typical examples of such embodiments are as follows:

(a) The culture products obtained from the above-mentioned method (1), or the reaction mixtures obtained from the above-mentioned method (2) or (3);

(b) The liquid mixtures obtained by removing the cultured cells from the culture products of the above-mentioned method (1) or the reaction mixtures of the above-mentioned method (2) or (3);

(c) The mixtures containing fatty acids or the fatty acid mixtures separated from (and optionally purified to any extent) the culture products of the above-mentioned method (1), the reaction mixtures of the above-mentioned method (2) or (3), or the above-mentioned liquid mixtures (b).

In the practice of the above-mentioned embodiment (b), any separation or isolation technique conventionally used for separating or isolating cells from culture products or reaction products containing the cells can be used. Furthermore, in the practice of the above-mentioned embodiment (c), any conventional technique generally used in the separation and recovery of fatty acids contained in aqueous media can be used. For example, the cultured mixtures or reaction mixtures obtained from the interaction of the *Staphylococcus capitis* with the fats and oils are directly used for recovering fatty acids therefrom. However, when the cultured mixtures, which are obtained from the culture media containing as a main raw material soybean-cake or other materials which remain as a solid substance after the culturing, are used, the remaining solid contents are desirably removed from the cultured mixture together with a total or partial amount of the cultured cells. The recovery of the fatty acids from the above-mentioned cultured mixtures, reaction mixtures, or solid content removal mixtures obtained above can be advantageously effected by an extraction method from the commercial point of view. Any extraction solvent which can dissolve the desired fatty acids but is not substantially missible with water can be used. Examples of such extraction solvents are ethyl acetate, ether, chloroform, benzene, and hexane. These solvents can be used alone or in any mixture thereof during the extraction.

The extracts are then evaporated to remove the extraction solvents therefrom. The resultant residues can be used as an active ingredient in the hair tonic composition according to the present invention. However, when further purification of the active ingredients is desired, any conventional methods for purifying organic compounds having an acid group can be used. For example, the above-mentioned organic extracts are mixed with aqueous basic media such as basic buffers to form the salts of the desired active ingredients, whereby the active ingredients in the form of the salts are transferred into the aqueous phase in the dissolved form and, if desired, these active ingredients in the aqueous media can be again extracted with the organic extraction solvent under an acidic condition. Alternatively, the crude products containing active ingredients are adsorbed by adsorbents such as silica gel and the adsorbed products can be separately eluted by solvents such as chloroform and benzene, alone or in any mixture.

As mentioned above, it is considered that there is a close correlation between the hair growth and the lipase activity and 5α-reductase inhibitory activity of the hair tonic composition applied to the surface of the scalp. The interaction products (i.e., the active ingredients) obtained from the interaction of *Staphylococcus capitis* with the vegetable or animal fats and oils have the 5α-reductase inhibitory activity, or both the 5α-reductase inhibitory activity and lipase activity. That is, active ingredients of the above-mentioned embodiments (a) and (b) have both the 5α-reductase inhibitory activity and lipase activity, whereas the active ingredients of the above-mentioned embodiment (c) do not have the lipase activity but have a strong 5α-reductase inhibitory activity due to the presence of concentrated fatty acids. These active ingredients of the above-mentioned embodiments (a), (b) and (c) can be most suitably used depending upon their characteristics in view of the properties of the base materials of the hair tonic compositions.

The amounts of the products (i.e., the active ingredients) obtained from the interaction of *Staphylococcus capitis* with the fats and oils largely depend upon the types of the active ingredients of the embodiments (a), (b), and (c), the types of the base materials of the hair tonic compositions, and the final forms of the hair tonic compositions. For example, the hair tonic composition of the present invention preferably includes 0.1% to 20% by weight of the active ingredients based on the weight of the hair tonic composition in the case of the above-mentioned embodiment (a) or (b). In the case of the active ingredients of the above-mentioned embodiment (c), the active ingredients are preferably included in an amount of 0.01% to 10% by weight based on the weight of the hair tonic composition depending upon the purification degree of the fatty acids.

The hair tonic compositions of the present invention comprise the active ingredients of the above-mentioned embodiments (a), (b), or (c) contained in any conventional base materials of the hair tonic compositions. Examples of such base materials are as follows:

(I) Water or aqueous solutions;
(II) Aqueous alcoholic solutions mainly containing alcohols; and
(III) Propylene glycol, liquid paraffin, ceresin, and petroleum jelly such as VASELINE.

When the active ingredients of the above-mentioned embodiments (a) or (b) are incorporated into the hair tonic compositions to effectively utilize the lipase activity thereof, the above-mentioned base materials (I) are preferably used. On the other hand, when the 5α-reductase inhibitory activity is desired to be utilized, any base materials of cosmetic compositions can be used without limitation. For example, the above-mentioned base materials (I), (II), and (III) can be used alone or in any combination (e.g., solutions, emulsions).

In addition to the above-mentioned active ingredients, various conventional ingredients suitably used in the formulation of a hair tonic composition or a hair dressing composition can be incorporated in a conventional amount into the hair tonic composition of the present invention. Typical examples of such ingredients are cantharis tincture, Jaborandi tincture, Japanese green gentian (Swertia Japonica) extract, follicle hormones, vitamin E, nicotinic acid derivatives, other vitamins such as vitamin B groups, amino acids such as serine and methionine, acetyl choline derivatives, cepharanthine, photosensitizing dyes, menthol, salicylic acid, resorcinol, beeswax, cetanol, triethanol amine, borax, lower alcohol esters of $C_{14}$ to $C_{18}$ saturated fatty acids, cetanol amine, glycerol monostearate, glycerol, isopropyl myristate, castor oil, citric acid, plant gums, and perfumes. These ingredients can be optionally incorporated into the hair tonic composition of the present invention unless the desired effect of the present invention is impaired.

The final forms of the hair tonic composition according to the present invention can be any conventional form of hair tonic or hair dressing compositions, such as hair lotion, hair cream, hair liquid, hair oil, pomade, and hair stick. Other forms can also be utilized.

Various theories have been proposed relating to the causes of depilation, epilation, dandruff, and itching. For example, an unbalanced hormone constitution theory, a nutrient relating theory, a seborrhea theory, and a genetic or hereditary theory are known, and it appears that there is a high correlation between the above-mentioned abnormal conditions and the development of glandula sebacea (see Masumi Inaba, "Mainichi Life" November, 1981, pages 26 to 35; "Saishin Keshohin Kagaku (Recent Cosmetics Science)", pages 130 published by Yakuji Nippo Sha in 1980; Kenji Adachi et. al., "Biochemical and Biophysical Research Communication, 41 (4), pages 884 to 890 (1970); Susumu Takayasu et. al., Journal of Investigative Dermatology 74, pages 187 to 191, 1980).

That is, when the glandula sebacea of a head portion is developed by nutrients, hormones or the like, testosterone is converted to stronger 5α-dihydrotestosterone by 5α-reductase present in the glandula sebacea. This is transferred to hair papilla via blood vessels, thereby alleviating the activities of adenylcyclase in hair-matrix cells. As a result, it is believed that the size of hair-follicles is gradually reduced causing involution and, therefore, the hair becomes thin and downy, eventually leading to baldness.

On the other hand, dandruff is formed because selium is selected and exudated to the surface of scalp in a large amount, due to the hypertrophy of glandula sebacea, and is mixed with horney or keratin peeled from the surface of the scalp. The dandruff thus formed inhibits dermal or skin respiration and the intake of nutrients into the fibril (or hair-root) portions. This also causes baldness.

Based on these mechanisms for generating depilation, epilation, and dandruff, the lipase activity, which decompose the lipid from the glandula sebacea, and the 5α-reductase inhibitory activity are important and essential characteristics and properties which the hair tonic compositions should have. These activities also become one standard or criterion for scientifically evaluating the effect of the hair tonic or hair dressing compositions.

As mentioned above, the microorganisms belonging to *Staphylococcus capitis* used in the present invention have a lipase activity and a 5α-reductase inhibitory activity, and produce fatty acids having a strong 5α-reductase inhibitory activity when the lipase is allowed to interact with lipids or fats and oils. Accordingly, when the culture products or the reaction products of the above-mentioned embodiment (a) or the cell removed liquid thereof of the above-mentioned embodiment (b) are used as an active ingredient of the hair tonic composition according to the present invention, the hair tonic composition has a lipase activity and a strong 5α-reductase inhibitory activity. On the other hand, when the fatty acids recovered from the culture products, the reaction mixture, or the cell removed liquid thereof are used as an active ingredient, the resultant hair tonic composition has a strong 5α-reductase inhibitory activity.

According to the experiment system adopted by the inventors, the recovered products containing the fatty acids isolated from the culture products have a 50% inhibitory concentration of 1.7 mM against 5α-reductase. These fatty acids can inhibit 50% of the activity of the 5α-reductase in a concentration of 0.01% to 0.04%.

The hair tonic composition according to the present invention can alleviate the generation of dandruff and itching due to the fact that the active ingredients thereof have the above-mentioned 5α-reductase inhibitory activity or both the above-mentioned lipase activity and 5α-reductase inhibitory activity. Furthermore, the microflora of the scalp is maintained in or brought to a healthy state by the fatty acids contained in the hair tonic composition according to the present invention (these fatty acids are formed by the interaction of *Staphylococcus capitis* with the fats and oils) and/or the fatty acids formed by decomposing the lipids from the glandula sebacea with the lipase contained in the hair tonic composition according to the present invention. It is considered that when these actions or functions are combined or multiplied they exhibit a strong hair growth acceleration effect.

The hair tonic composition according to the present invention has the 5α-reductase inhibitory activity or both the 5α-reductase inhibitory activity and lipase activity as mentioned above. When the hair tonic composition according to the present invention is applied to the human scalp downy hairs become healthy and the generation of dandruff and itching can be prevented.

The nonpathogenicity of the hair tonic composition according to the present invention has been confirmed. That is, the above-mentioned culture product and the purified fatty acids recovered therefrom were independently dispersed in an ethanol and the mixtures were spread on the skins of five rabbits once a day for 3 days in each dispersion. The ethanol was also spread in the same manner as a control. As a result, no abnormal condition was found in each case, as shown in Table 1.

TABLE 1

| Test dispersion | Irritation score |
|---|---|
| Control | 0 |
| 0.2% aqueous alcohol solution of the culture product | 0 |
| 0.02% aqueous alcohol solution of the fatty acids | 0 |

EXAMPLES

The present invention will now be further illustrated by, but is by no means limited to, the following examples, in which the preparation, application, and effect of the hair tonic composition of the present invention are specifically disclosed.

EXAMPLE 1

Preparation of Active Ingredient

A 10 liter amount of a culture medium containing 10 g/liter of peptone, 5 g/liter of yeast extract, 1 g/liter of glucose, and 5 g/liter of sodium chloride was placed in a 20 liter jar fermentor and was then sterilized at a temperature of 120° C. for 15 minutes in an autoclave. *Staphylococcus capitis* ATCC 27840 cells were inoculated into the above culture medium in a concentration of $1 \times 10^6$ cells/ml and this was aerobically precultured at a temperature of 35° C. for 12 hours while agitating.

A 100 liter amount of the liquid culture medium having the same composition as mentioned above was charged into a fermentor having a charge capacity of 100 liters, and 5 liters of olive oil was then added to the liquid culture medium. After the liquid culture medium was sterilized at a temperature of 120° C. for 15 minutes, 1 liter of the preculture product was added to the sterilized medium and was aerobically cultivated at a temperature of 35° C. for 20 hours while stirring under aeration.

A portion of the cultured product was subjected to a centrifugal separation treatment, whereby solid cells were removed therefrom. Thus, the supernatant solution was obtained.

A 10 g amount of sodium chloride was dissolved in 100 ml of the supernatant solution obtained above and 100 ml of ethyl acetate was added thereto. The mixture was thoroughly stirred and the separated ethyl acetate layer was recovered. The ethyl acetate layer was concentrated to dryness. The resultant residue was dissolved in methanol and the methanol solution was again concentrated to dryness. The residue thus obtained was dissolved in benzene. The benzene solution was treated with a silica gel column chromatography. The elution was carried out by using benzene, a mixture of benzene and chloroform (1:1 V/V), and chloroform, in that order. The chloroform eluate was concentrated to obtain the active ingredient containing fatty acids.

The lipase activity and 5α-reductase inhibitory activity of the above-mentioned culture products and the recovered and purified active ingredient were determined as follows:

Determination of Lipase Activity

A 4.5 ml amount of a Tris-hydrochloric acid buffer solution (pH=8.0), 1 ml of a 1/10M calcium chloride solution, 1 g of a substrate (olive oil or tributyrin), and 1 g or 1 ml of a sample were mixed together and the mixture was allowed to react at a temperature of 30° C. for 1 hour while shaking. The amount of the formed fatty acids was titrated with a 1/20M potassium hydroxide solution.

The results are as follows:

| Lipase Activity (Culture Product) | |
|---|---|
| Substrate | Activity |
| Olive oil | 0.06 unit ($\mu$mol/min · ml) |
| Tributyrin | 0.04 unit ($\mu$mol/min · ml) |

Determination of 5α-Reductase Inhibitory Activity

Prostate gland cells of rats were crushed and a specimen of testosterone 5α-reductase was then prepared by separating microsome from the crushed liquid mixture. The conversion of testosterone to 5α-dihydrotestosterone by the use of the above-prepared enzyme specimen was monitored by radioisotopically labelled testosterone. The reaction mixture was extracted with ethyl acetate and the extract was developed twice by silica gel thin layer chromatography (solvent system, dichloromethane:cyclohexane:acetone=15:4:1). The amount of 5α-dihydrotestosterone were determined from the intensities of the radioactivity.

Reaction

A 30 $\mu$l amount of a 0.05M phosphate buffer (pH=6.6) containing 0.1% of BSA (bovine serum albumin), 10 μl of an enzyme specimen, 8.5 pmol of labelled testosterone, 50 nmol of a reduced form of NADP (nicotinamide adenine dinucleotide phosphate), and 10 μl of a test sample were mixed (total amount=50 μl). The mixture was allowed to react at a temperature of 25° C. for 60 minutes.

After the completion of the reaction, the reaction mixture was extracted with ethyl acetate by adding 50 μl of ethyl acetate to the reaction mixture. The extract was developed in the same manner as mentioned above and the intensity of the radioisotope was measured by using a scintillation counter.

The above-mentioned determination was applied to the samples having various concentrations. The 5α-reductase inhibitory activity was obtained as a inhibitory rate (%) or a 50% inhibitory concentration.

The results are as follows:

| | 5α-Reductase inhibitory activity | |
|---|---|---|
| Test sample | Radioactivity of 5α-dihydrotestosterone and adiols*[3] | 5α-Reductase inhibitory rate (%) |
| Culture product of Example 1 | 242 dpm | 98% |
| Control (1)*[1] | 12591 dpm | — |
| Control (2)*[2] | 13357 dpm | 0% |

*[1] A phosphate buffer solution was used as a test sample.
*[2] A culture product obtained by culturing *Staphylococcus epidermidis* in the same culture medium as used in Example 1.
*[3] Since a portion of the formed 5α-dihydrotestosterone was further converted to adiols (3α- and 3β- 17β- androstanediols), the radioactivity of the adiols was also counted.

As is clear from the results shown above, the culture products of the present invention have a strong 5α-reductase inhibitory activity. The 50% inhibitory concentration of the fatty acid mixture obtained in Example 1 was 1.7 mM.

The fatty acid composition of the active ingredient in Example 1 determined by chromatography was as follows:

TABLE 2

| Fatty acid | Content (wt. %) |
|---|---|
| Palmitic acid | 1.3 |
| Palmitoleic acid | 0.2 |
| Stearic acid | 2.0 |
| Oleic acid | 65.7 |
| Linolic acid | 18.0 |
| Linolenic acid | 0.8 |

Of these fatty acids, palmitic acid, palmitoleic acid, oleic acid, and linolic acid have an especially strong 5α-reductase inhibitory activity. Accordingly, fats and oils containing either one of these fatty acids can be used in the present invention.

EXAMPLE 2

*Staphylococcus capitis* ATCC-27840 was cultivated in the same manner as in Example 1, except that a culture medium comprising 50 g/l of soybean peptone and 5 g/l of sodium chloride was used. The solid contents were centrifugally removed from the culture products to obtain the supernatant solution. The lipase activity of the supernatant solution determined according to the above-mentioned method is as follows:

TABLE 3

| Substrate | Activity |
|---|---|
| Olive oil | 4.00 unit (μmol/min · ml) |

TABLE 3-continued

| Substrate | Activity |
|---|---|
| Tributyrin | 3.10 unit (μmol/min · ml) |

A 500 g amount of sodium chloride was dissolved in about 10 liters of the supernatant solution obtained above and the solution was extracted with 10 liters of chloroform. The chloroform extract solution was concentrated in vacuo to obtain an oily product.

The oily product thus obtained was extracted with hexane and the hexane extract was then adsorbed to an adsorption column containing 1 kg of silica gel packed therein. The elution was carried out by using benzene, a mixture of benzene and chloroform (1:1 V/V), chloroform, a mixture of chloroform and methanol (1:1 V/V), and methanol, in this order.

The lipase activity and the 5α-reductase inhibitory activity of each elution fraction were determined according to the above-mentioned method. The results are as follows:

TABLE 4

| Eluate | Lipase Activity | Distribution (%) of 5α-reductase inhibitory activity |
|---|---|---|
| Benzene | 0 | 0 |
| Benzene-chloroform | 0 | 0 |
| Chloroform | 0 | 82 |
| Chloroform-methanol | 0 | 18 |
| Methanol | 0 | 0 |

EXAMPLE 3

A 10 liter amount of a culture product was obtained in the same manner as the preculture in Example 1. The culture product was centrifugally separated to obtain cells. The cells thus obtained were suspended in 100 ml of a 0.02M phosphate buffer (pH=7.0). 10 g of tallow and 2 g of calcium chloride were added to the suspension and the mixture was stirred at a temperature of 30° C. for 24 hours. Thus, the cells were incubated with the tallow.

The lipase activity and the 5α-reductase inhibitory activity (cell removed liquid) gradually increased as follows:

TABLE 5

| Time (hr) | Lipase activity unit (μmol/min · ml) | 5α-Reductase inhibitory activity (unit/ml)*[1] |
|---|---|---|
| 0 | 1.0 | 0 |
| 12 | 2.3 | 120 |
| 24 | 5.0 | 290 |

*[1] The amount in which 50% of 5α-reductase activity under the experimental condition was inhibited is defined as 1 unit.

EXAMPLE 4

(Preparation form)

The following hair tonic compositions were formulated:

| | Content (Vol. %) |
|---|---|
| (1) Lotion type: Ingredient | |
| Culture product (Example 1) | 10.0 |
| Perfume | 1.0 |

-continued

| | |
|---|---|
| Preservative (5% sodium salicylate solution) | 1.0 |
| Distilled water | to 100 |

| | Content (wt %) |
|---|---|
| (2) Hair Cream type: Ingredient | |
| Liquid paraffin | 50.0 |
| Polyethylene glycol | 1.0 |
| Tween 20 | 0.1 |
| Reaction mixture (Example 3) | 1.0 |
| Distilled water | to 100 |
| (3) Hair Tonic type: Ingredient | |
| Ethyl alcohol | 80.0 |
| Fatty acids (Example 2) | 0.2 |
| Distilled water | to 100 |
| (4) Aerosol type Ingredient | |
| Polyoxyethylene lanolin | 1.0 |
| Lanolin alcohol | 2.5 |
| Glycerol fatty acid ester | 0.5 |
| Perfume | 0.2 |
| Fatty acids (Example 2) | 0.62 |
| Distilled water | to 100 |

EXAMPLE 5

Application of Hair Tonic Composition (1) Application of hair tonic type composition to the human scalp The hair tonic type composition prepared in Example 4(3) was applied, twice a day, to the scalps of 10 men, each suffering from a large degree of itching, dandruff, and depilation at ages of 28 to 40, in an amount of 3 to 4 ml each for 6 months.

The results are as follows:

TABLE 6

| Condition | Excellent | Effect Good | None |
|---|---|---|---|
| Dandruff | 8 | 2 | 0 |
| Depilation | 0 | 7 | 3 |
| Itching | 10 | 0 | 0 |

(2) Application of hair tonic type composition to rabbits

Three month old male rabbits were shorn on the back. The hair tonic type composition prepared in Example 4(3) was applied, twice a day, to a half-side of the shorn portion of each rabbit for one week. As a control, the base material in Example 4(3) was also applied, twice a day, to the other half-side of the shorn portion of each rabbit for one week. The length of the grown fur was measured.

The results are as follows:

TABLE 7

| Rabbit No. | Grown fur length Control side a | Test side a' | Difference b |
|---|---|---|---|
| 1 | 2.50 ± 0.08 | 2.83 ± 0.05 | 0.33 |
| 2 | 2.41 ± 0.05 | 2.63 ± 0.08 | 0.22 |
| 3 | 2.50 ± 0.09 | 2.90 ± 0.10 | 0.40 |
| 4 | 3.04 ± 0.12 | 3.38 ± 0.08 | 0.34 |
| 5 | 2.96 ± 0.04 | 3.49 ± 0.05 | 0.53 |
| 6 | 2.22 ± 0.07 | 2.85 ± 0.05 | 0.63 |
| 7 | 2.29 ± 0.09 | 2.70 ± 0.08 | 0.41 |
| 8 | 4.02 ± 0.12 | 4.55 ± 0.09 | 0.53 |
| 9 | 2.38 ± 0.07 | 2.61 ± 0.04 | 0.23 |
| 10 | 2.47 ± 0.08 | 3.04 ± 0.10 | 0.57 |
| Average | 2.68*[1] | 3.10*[2] | 0.42 |
| Srandard error | — | — | 0.13 |

(Remarks)
a Average fur growth length of control side (mm) ± standard deviation
a' Average fur growth length of test side (mm) ± standard deviation
b Average fur growth length of test side - average fur growth length of control side (mm)
*[1] Mean value of average growth length of control side
*[2] Mean value of average growth length of test side As is clear from the results shown in Table above, the hair tonic composition according to the present invention increases the fur growth rate by 15% or more as compared with the control.

We claim:

1. A hair tonic composition comprising a product obtained from interaction of at least one member selected from the group consisting of vegetable and animal fats and oils with a microorganism belonging to Staphylococcus capitis at a cultivation temperature of between about 20° C. and about 40° C. and at a pH ranging from about 6 to about 9 under aerobic conditions, wherein said fats and oils are selected from the group consisting of olive oil, castor oil, cottonseed oil, coconut oil, soybean oil, palm oil, safflower oil, colza oil, rice bran oil, tsubaki oil, sesame oil, tallow, lard, mutton tallow, mink oil and whale oil, said product having 5α-reductase activity and being present in said composition in an amount effective to treat dandruff and itching.

2. The hair tonic composition as claimed in claim 1 wherein said product is obtained from interaction of 1 to 250 g/liter of fats and oils with said microorganism belonging to Staphylococcus capitis.

3. A hair tonic composition as claimed in claim 1, wherein said product is obtained by cultivating the microorganism belonging to Staphylococcus capitis in a culture medium and then contacting the cultured cells with the vegetable or animal fat or oil in an aqueous medium.

4. A method for preparing a hair tonic composition comprising incorporating into said hair tonic composition a product obtained from interaction of at least one member selected from the group consisting of vegetable and animal fats and oils with a microorganism belonging to Staphylococcus capitis at a cultivation temperature of from about 20° C. to about 40° C. and a pH of from about 6 to about 9 under aerobic conditions, wherein said fats and oils are selected from the group consisting of olive oil, castor oil, cottonseed oil, coconut oil, soybean oil, palm oil, safflower oil, colza oil, rice bran oil, tsubaki oil, sesame oil, tallow, lard, mutton tallow, mink oil and whale oil, said product having 5α-reductase activity and being present in said composition in an amount effective to treat dandruff and itching.

5. The method for preparing a hair tonic composition as claimed in claim 4 wherein said product is obtained from interaction of 1 to 250 g/liter of fats and oils with said microorganism belonging to Staphylococcus capitis.

6. A method as claimed in claim 4, wherein said products are obtained by cultivating the microorganism belonging to Staphylococcus capitis in a culture medium and then contacting the cultured cells with the vegetable or animal fat or oil in an aqueous medium.

7. A method for depressing the generation of dandruff and itching in the hair and scalp comprising applying to the hair and scalp a hair tonic composition containing a product obtained from interaction of at least one member selected from the group consisting of vegetable and animal fats and oils with a microorganism belonging to *Staphylococcus capitis*, at a cultivation temperature of between about 20° C. and about 40° C. and a pH of between about 6 to about 9 under aerobic conditions, wherein said fats and oils are selected from the group consisting of olive oil, castor oil, cottonseed oil, coconut oil, soybean oil, palm oil, safflower oil, colza oil, rice bran oil, tsubaki oil, sesame oil, tallow, lard, mutton tallow, mink oil, and whale oil, said product having 5α-reductase activity and being present in an amount effective to treat dandruff and itching.

8. The method for depressing the generation of dandruff and itching in the hair and scalp as claimed in claim 7 wherein said product is obtained from the interaction of 1 to 250 g/liter of fats and oils with said microorganism belonging to *Staphylococcus capitis*.

* * * * *